(12) United States Patent
Dikeman

(10) Patent No.: US 8,974,501 B2
(45) Date of Patent: Mar. 10, 2015

(54) DISTAL LOADING RECEIVER FOR A POLYAXIAL BONE SCREW AND METHOD FOR IMPLANTATION THEREOF

(75) Inventor: Sean Dikeman, Solana Beach, CA (US)

(73) Assignee: Alphatec Spine, Inc., Carlsbad, CA (US)

( * ) Notice: Subject to any disclaimer, the term of this patent is extended or adjusted under 35 U.S.C. 154(b) by 157 days.

(21) Appl. No.: 13/274,203

(22) Filed: Oct. 14, 2011

(65) Prior Publication Data

US 2012/0095516 A1    Apr. 19, 2012

Related U.S. Application Data

(60) Provisional application No. 61/394,183, filed on Oct. 18, 2010.

(51) Int. Cl.
*A61B 17/70* (2006.01)
(52) U.S. Cl.
CPC ......... *A61B 17/7037* (2013.01); *A61B 17/7032* (2013.01)
USPC ............ 606/267; 606/264; 606/300; 606/305
(58) Field of Classification Search
CPC . A61B 17/7032; A61B 17/8605; A61B 17/84
USPC ........................ 606/246, 264–279, 300–321
See application file for complete search history.

(56) References Cited

U.S. PATENT DOCUMENTS 8,167,910 B2 * 5/2012 Nilsson .......................... 606/264

* cited by examiner

*Primary Examiner* — Mary Hoffman
*Assistant Examiner* — Christina Negrellirodrigue
(74) *Attorney, Agent, or Firm* — Michael J. Loi

(57) ABSTRACT

A distal loading receiver for a polyaxial bone screw includes a body member having a circumferential wall defining a bore disposed longitudinally through the body member. A skirt depends from a distal end of the body member. The skirt defines one or more distally opening slots and an abluminal surface of the skirt includes one or more transverse ribs proximate to a distal end of the skirt. A retaining ring includes a luminal surface having one or more transverse recesses proximate to a distal end of the luminal surface and one or more walls extending inwardly from the luminal surface. The slots accommodate the walls and the recesses accommodate the ribs to attach the body member to the retaining ring when the distal end of the skirt is inserted into a proximal end of the retaining ring.

14 Claims, 5 Drawing Sheets

US 8,974,501 B2

DISTAL LOADING RECEIVER FOR A POLYAXIAL BONE SCREW AND METHOD FOR IMPLANTATION THEREOF

CROSS-REFERENCE TO RELATED APPLICATIONS

This application claims priority to U.S. Provisional Patent Application No. 61/394,183, filed Oct. 18, 2010, which is incorporated herein by reference.

FIELD

The present invention relates generally to an apparatus for internal fixation of the spine and, more specifically relates to a distal loading receiver for a polyaxial bone screw that may be assembled in situ.

BACKGROUND

Certain spinal conditions, including a fracture of a vertebra and a herniated disc, indicate treatment by spinal immobilization. Several systems of spinal joint immobilization are known, including surgical fusion and the attachment of pins and bone plates to the affected vertebras. Known systems include screws having proximal heads and threaded shafts that may be inserted into at least two spaced-apart vertebras. Each screw includes a receiver attached over the head such that a stabilization rod can interconnect two or more receivers to immobilize the vertebras spanned by the screws. However, in these systems, the shaft is disposed through the receiver from a proximal or top side of the receiver; thus, the receiver is attached over the threaded shaft before the shaft is inserted into a vertebra.

During surgical implantation of spinal immobilization systems, the surgical site is crowded with tissue masses, sponges, and other surgical implements that may obstruct access to the sites of implantation of the threaded shafts. Further, because the receivers are necessarily larger than the heads of the screws, it can be difficult to maneuver around the receivers of prior implanted screws to implant a subsequently implanted screw near the prior implanted screws. Current spinal immobilization systems would therefore benefit from a distal loading receiver for a polyaxial bone screw including a receiver that can be attached over a generally rounded proximal head of a threaded shaft subsequent to the implantation of the threaded shaft.

Thus, the present invention helps to alleviate a lack of space at the site of implantation of a spinal immobilization system as compared to the prior art, allowing the surgeon additional freedom in locating the threaded shafts of polyaxial bone screws closer together than previously possible. The result is a significantly improved distal loading receiver for a polyaxial bone screw.

SUMMARY

An exemplary distal loading receiver for a polyaxial bone screw includes a body member having a circumferential wall defining a bore disposed longitudinally through the body member. A skirt depends from a distal end of the body member. The skirt defines one or more disposed distally opening slots and an abluminal surface of the skirt includes one or more transverse ribs proximate to a distal end of the skirt. A retaining ring includes a luminal surface having one or more transverse recesses proximate to a distal end of the luminal surface and one or more walls extending inwardly from the luminal surface. The slots accommodate the walls and the recesses accommodate the ribs to attach the body member to the retaining ring when the distal end of the skirt is inserted into a proximal end of the retaining ring.

In other features, the skirt is adapted to expand from a rest state to receive a bone screw having a proximal head that is larger in diameter than the bore at the distal end of the skirt in the rest state. The circumferential wall includes a pair of oppositely disposed proximally opening slots that each includes a rounded distal end. The distal loading receiver further includes a bushing disposed within the bore and including a second pair of oppositely disposed proximally opening slots and a second distally depending skirt. The second pair of oppositely disposed proximally opening slots is adapted to accommodate a fixation rod, and the second distally depending skirt is adapted to abut a periphery of the proximal head. The distal loading receiver further includes the bone screw having a proximal head that is larger in diameter than the bore at the distal end of the skirt in the rest state. An abluminal surface of the skirt depending from the distal end of the body member is diametrically constricted relative to the body member. The retaining ring includes an annular wall extending inwardly from the luminal surface distal to the transverse recesses.

An exemplary polyaxial screw assembly including a distal loading receiver includes a polyaxial screw having a proximal head and a threaded shaft. A body member includes a circumferential wall defining a bore for receiving the polyaxial screw. The circumferential wall includes a first pair of oppositely disposed proximally opening slots that each includes a rounded distal end. A first skirt depends from a distal end of the body member. The first skirt defines one or more distally opening slots and an abluminal surface of the first skirt includes one or more transverse ribs proximate to a distal end of the first skirt. A retaining ring includes a luminal surface having one or more transverse recesses proximate to a distal end of the luminal surface and one or more walls extending inwardly from the luminal surface. The slots accommodate the walls and the recesses accommodate the ribs to attach the body member to the retaining ring when the distal end of the first skirt is inserted into a proximal end of the retaining ring.

In other features, the polyaxial screw assembly further includes a bushing disposed within the bore and including a second pair of oppositely disposed proximally opening slots and a second distally depending skirt. The second pair of oppositely disposed proximally opening slots is adapted to accommodate a fixation rod, and the second distally depending skirt is adapted to abut a periphery of a proximal head of a bone screw. The first skirt is adapted to expand from a rest state to receive the polyaxial screw. The proximal head is larger in diameter than the bore at the distal end of the skirt in the rest state. An abluminal surface of the first skirt is diametrically constricted relative to the body member. The retaining ring includes an annular wall extending inwardly from the luminal surface distal to the transverse recesses.

An exemplary method for assembling a polyaxial screw assembly that includes a polyaxial screw, a body member, and a retaining ring, includes the step of placing the retaining ring over a proximal head of the polyaxial screw, the retaining ring including a luminal surface having one or more recesses proximate to a distal end of the luminal surface and one or more walls extending inwardly from the luminal surface. The method further includes the step of aligning a bore of the body member with the proximal head of the polyaxial screw, the body member having a circumferential wall defining the bore disposed longitudinally through the body member The method further includes the step of forcing a distal end of a skirt depending from a distal end of the body member into a proximal end of the retaining ring, the skirt defining one or more distally opening slots and an abluminal surface of the skirt including one or more transverse ribs proximate to a distal end of the skirt. The slots of the skirt accommodate the walls of the retaining ring and recesses of the retaining ring accommodate the ribs of the skirt to attach the body member to the retaining ring.

In other features, the method further includes the step of inserting a bushing into the distal end of the body member, the bushing including a second pair of oppositely disposed proximally opening slots and a second distally depending skirt. The second pair of oppositely disposed proximally opening slots is adapted to accommodate a fixation rod. The method further includes the step of first inserting the polyaxial screw into a vertebra prior to placing the ring over the proximal head, aligning the bore of the body member with the proximal head, and forcing the distal end of the skirt into the ring.

DETAILED DESCRIPTION

Figure 1:
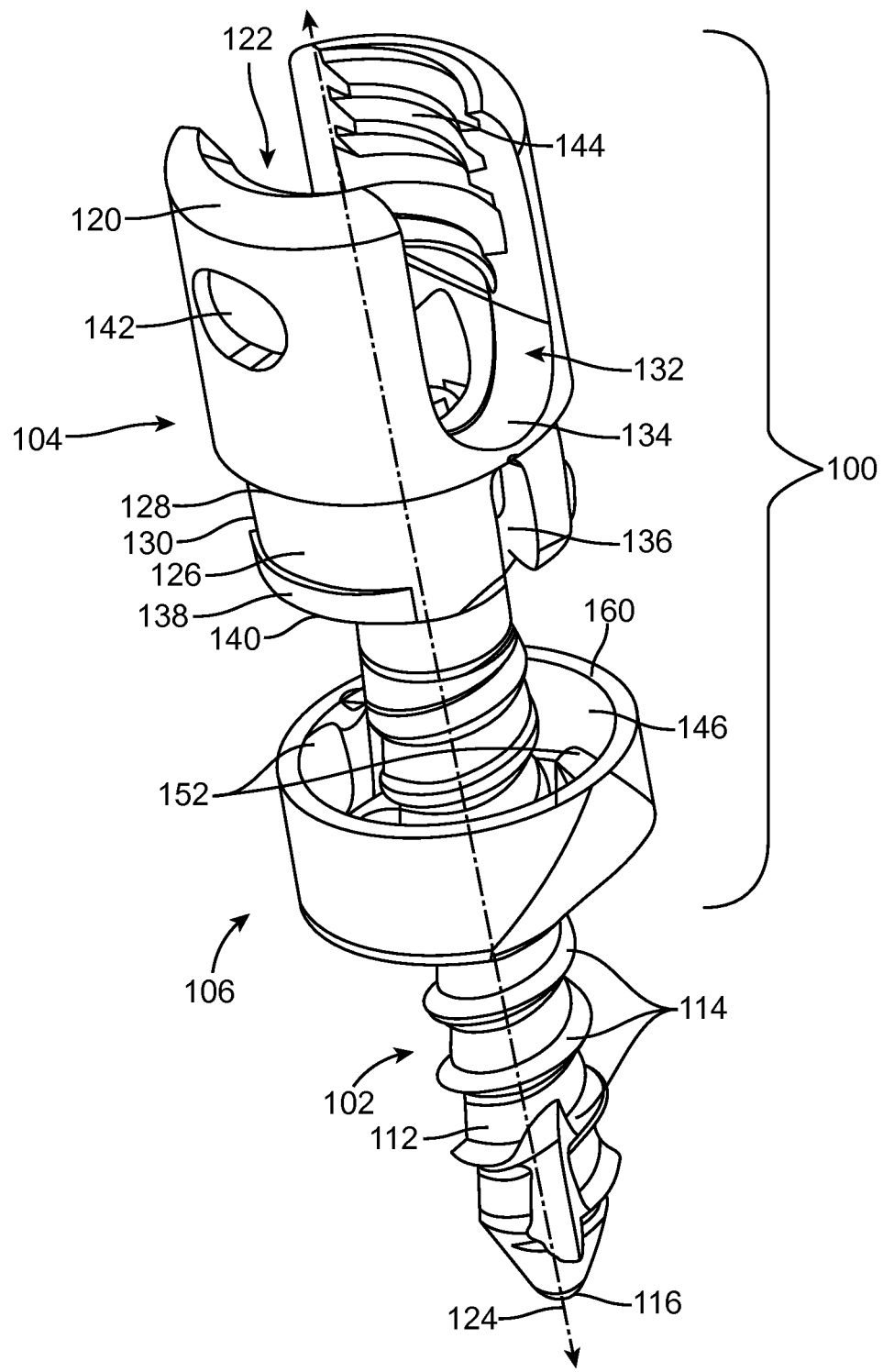
FIG. 1 is an isometric view of an embodiment of a distal loading receiver.

The foregoing and other features and advantages of the invention are apparent from the following detailed description of exemplary embodiments, read in conjunction with the accompanying drawings in which like structural or functional elements may be designated by like reference numerals.

Embodiments of the invention will now be described with reference to the Figures, wherein like numerals reflect like elements throughout. The terminology used in the description presented herein is not intended to be interpreted in any limited or restrictive way, simply because it is being utilized in conjunction with detailed description of certain specific embodiments of the invention. Furthermore, embodiments of the invention may include several novel features, no single one of which is solely responsible for its desirable attributes or which is essential to practicing the invention described herein. The words proximal and distal are applied herein to denote specific ends of components of the instrument described herein. A proximal end refers to the end of an instrument nearer to an operator of the instrument when the instrument is being used. A distal end refers to the end of a component further from the operator and extending towards the surgical area of a patient and/or the implant.

Figure 2:
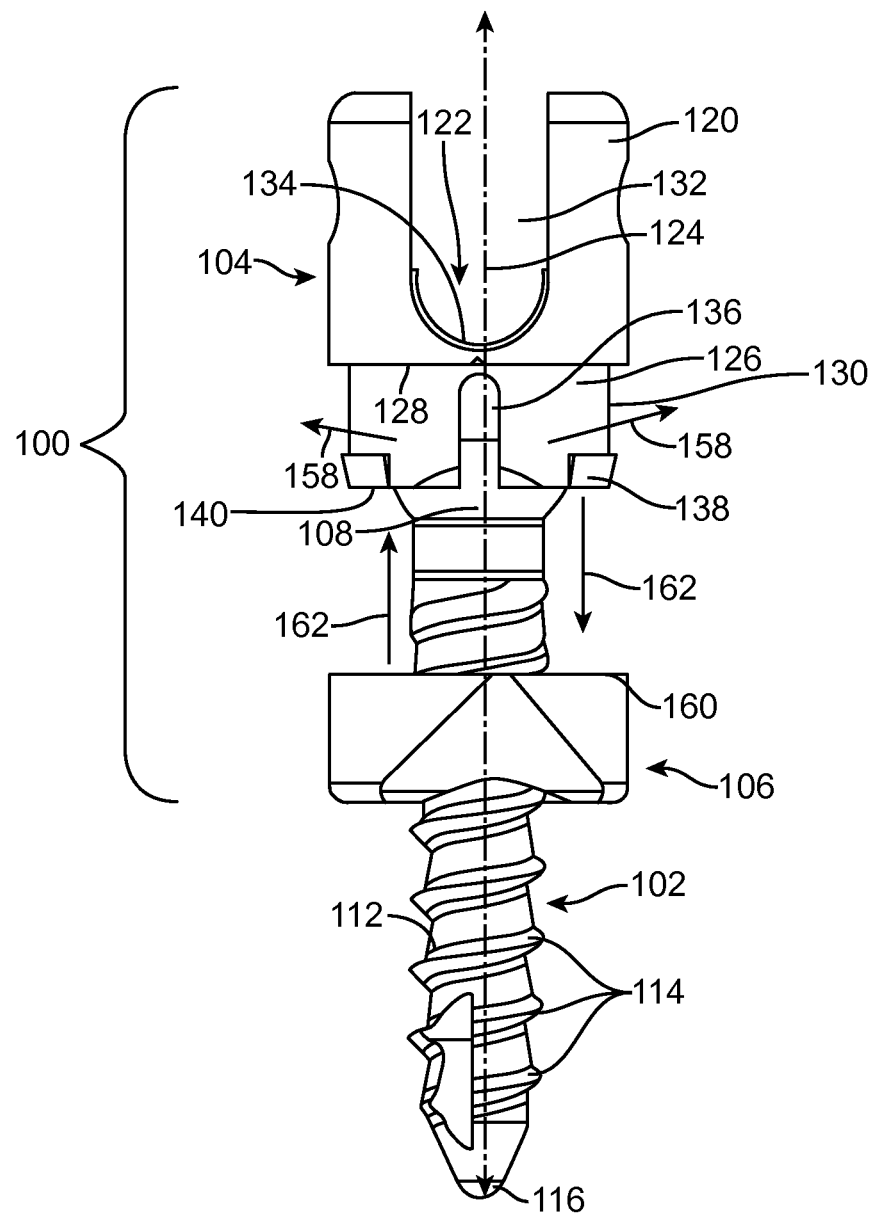
FIG. 2 is a side elevational view of the distal loading receiver of FIG. 1.

An embodiment of a distal loading receiver 100 for a polyaxial bone screw 102 includes a body member 104 and a retaining ring 106, as illustrated in FIGS. 1 and 2. The polyaxial bone screw 102 includes a proximal head 108 having a generally rounded surface 110 (see FIG. 3) and a shaft 112. The shaft 112 may include threads 114 and a distal end 116 that may be narrowed or pointed to facilitate entry into bone, as may be known in the art. A recess 118 disposed in a proximal surface of the proximal head 108 accommodates a tool for driving the shaft 112 into bone. Examples of polyaxial bone screws 102 that may be useful in the current invention may be found in Purcell et al. U.S. Patent Application Publication No. 2008/0243189 and Purcell et al. U.S. Pat. No. 7,377,923, which are both hereby incorporated by reference in their entirety herein.

Figure 3:
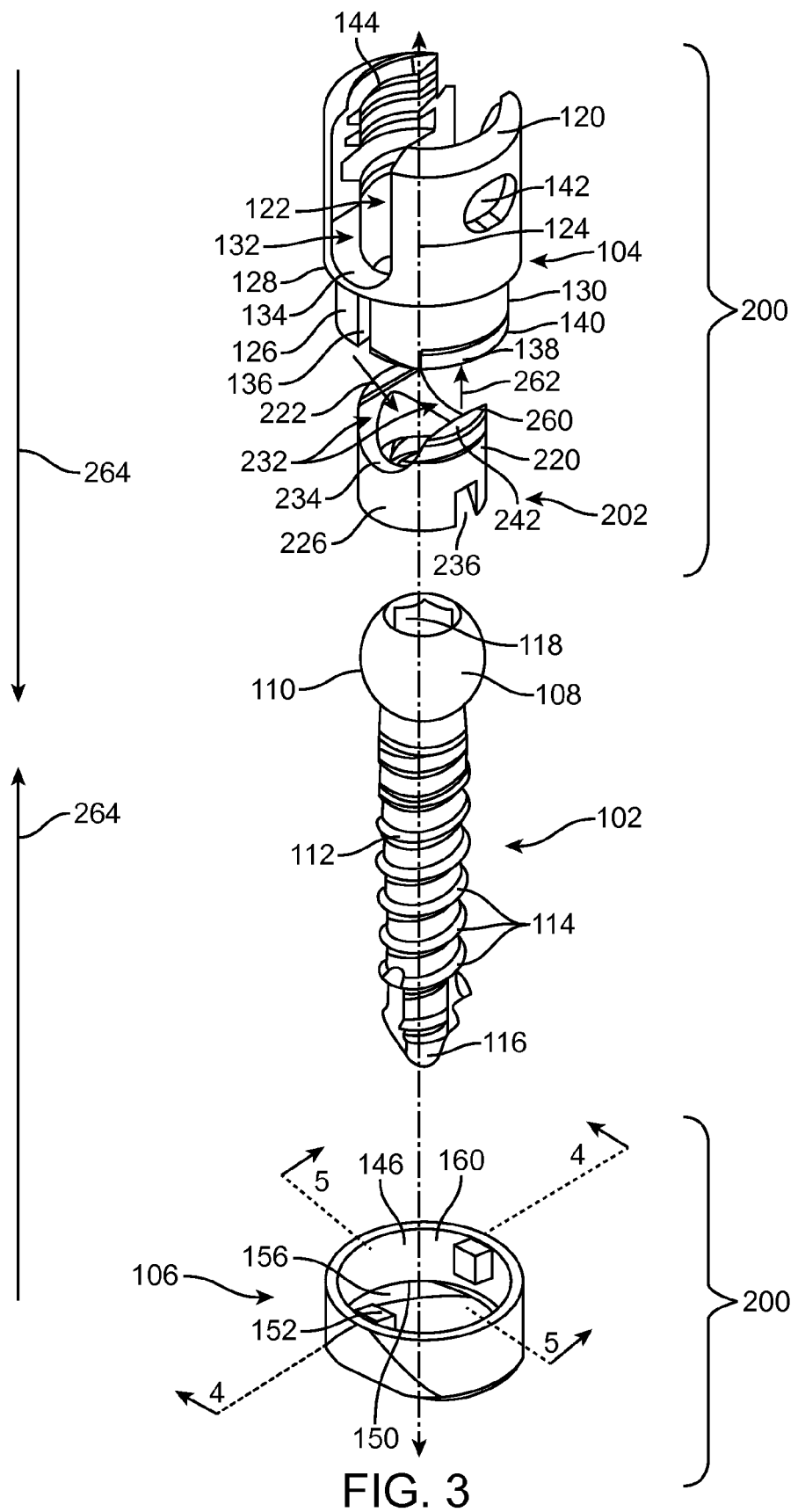
FIG. 3 is an isometric view of another embodiment of a distal loading receiver.

Referring to FIGS. 1 and 2, the body member 104 includes a circumferential wall 120 defining a bore 122 disposed along a longitudinal axis 124 through the body member 104. A skirt 126 depends from a distal end 128 of the body member 104. In this embodiment, an abluminal surface 130 of the skirt 126 depending from the distal end 128 of the body member 104 is diametrically constricted relative to the body member 104, i.e. includes a smaller diameter than the body member 104, as illustrated in FIGS. 1-3. In other embodiments, the skirt 126 may include an abluminal surface 130 that is generally flush with the body member 104 or that is diametrically expanded relative to the body member 104, i.e. includes a larger diameter than the body member 104.

Referring to FIGS. 1-3, the circumferential wall 120 includes a first pair of oppositely disposed proximally opening slots 132 that each includes a rounded distal end 134 for accommodation of a fixation rod (not shown) therein. Similarly, the skirt 126 defines a pair of oppositely disposed distally opening slots 136, which will be discussed in further detail herein below. The abluminal surface 130 of the skirt 126 includes a pair of oppositely disposed transverse ribs 138 proximate to a distal end 140 of the skirt 126.

Referring to FIGS. 1 and 3, some embodiments of the body member 104 may include one or more apertures or recesses 142 disposed within the circumferential wall 120. Further, threads or ratchets 144 may be disposed on an inner surface of the bore 122 to facilitate the attachment of a cap or set screw member (not shown). Examples of body members 104 or features thereof that may be useful in the current invention may be found in Purcell et al. U.S. Patent Application Publication No. 2008/0243189 and Purcell et al. U.S. Pat. No. 7,377,923, incorporated by reference herein.

Figure 4:
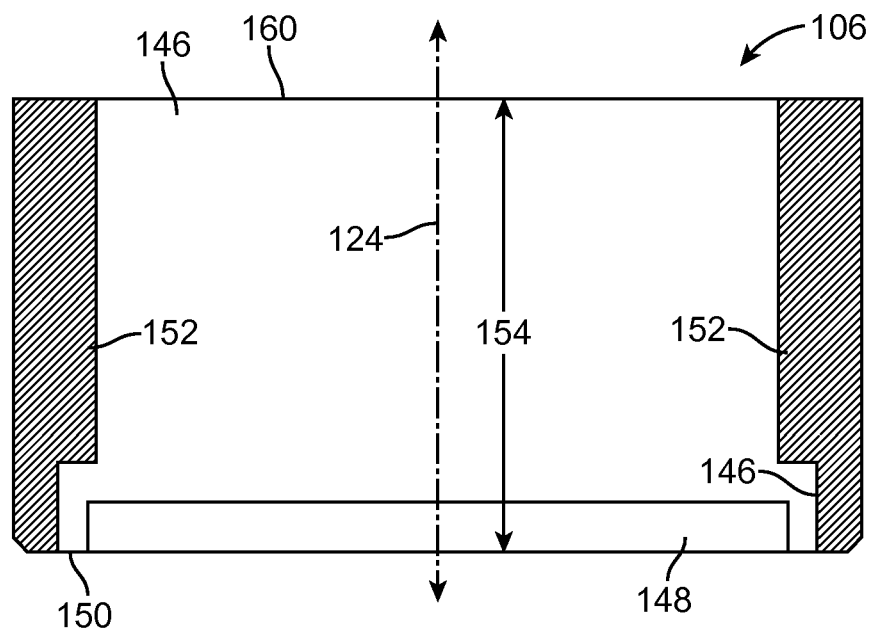
FIG. 4 is a cross-sectional view of an embodiment of a retaining ring, taken generally along the line 4-4 of FIG. 3.
Figure 5:
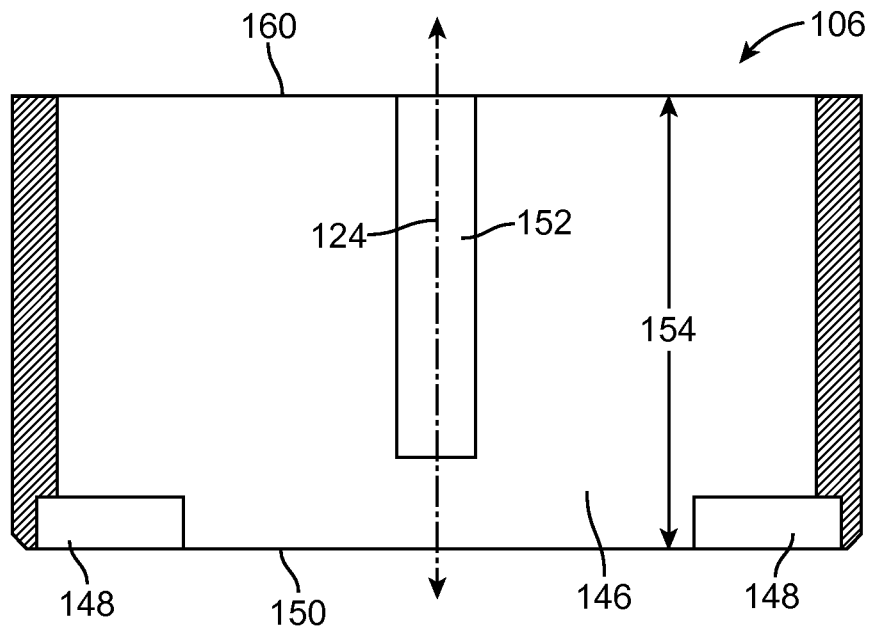
FIG. 5 is a cross-sectional view of the retaining ring of FIG. 3, taken generally along the line 5-5 of FIG. 3.
Figure 6:
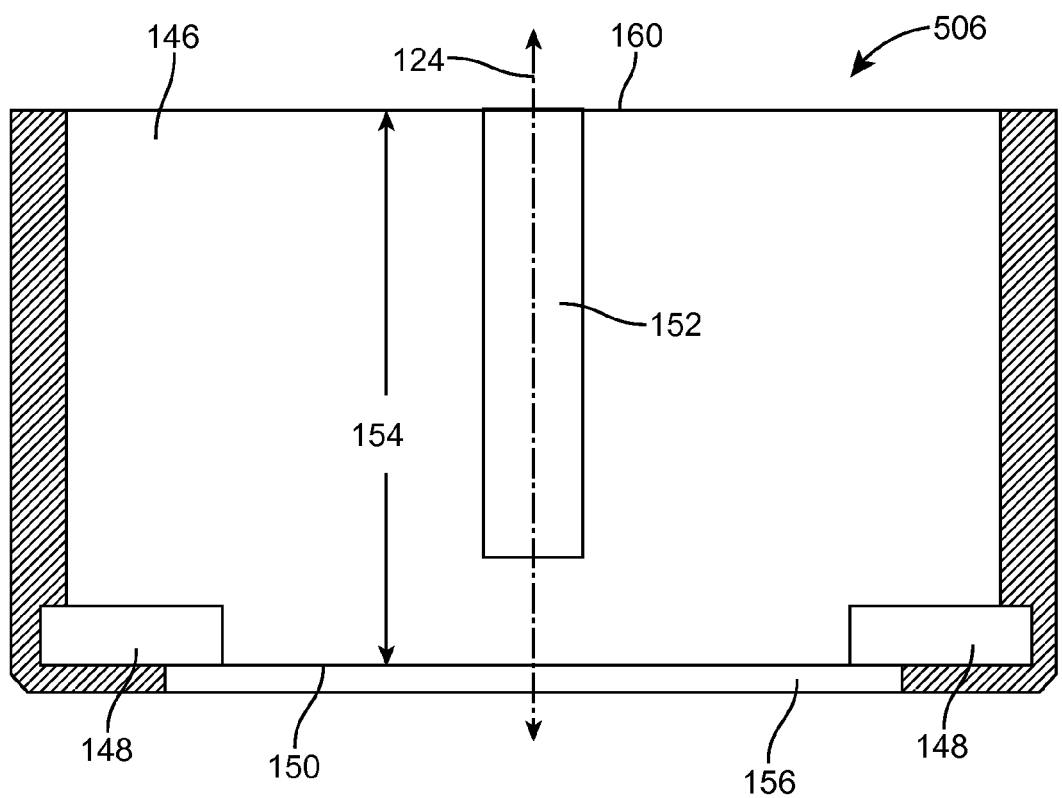
FIG. 6 is a cross-sectional view of an embodiment of a retaining ring, taken generally along the line 5-5 of FIG. 3.

The retaining ring 106 includes a luminal surface 146 having a pair of oppositely disposed transverse recesses 148 proximate to a distal end 150 of the luminal surface 146 and a pair of oppositely disposed walls 152 extending inwardly from the luminal surface 146, as illustrated in FIGS. 1, 3, 4, and 5. When the retaining ring 106 is engaged with the body member 104, the slots 136 accommodate the walls 152 and the recesses 148 accommodate the ribs 138, as described further herein below. In this embodiment, the walls 152 may have a longitudinal extent over a portion of the length 154 of the luminal surface 146, as illustrated in FIGS. 4 and 5. In other embodiments, the walls 152 may extend the entire length 154 of the luminal surface 146. In one embodiment, the retaining ring 106 includes an annular wall 156 extending inwardly from the luminal surface 146 distal to the transverse recesses 148, as best visible in FIG. 6.

The skirt 126 includes a rest-state where the pair of oppositely disposed distally opening slots 136 is in a relaxed and unexpanded state such that the bore 122 has a rest-state diameter at the distal end 140 of the skirt 126. In some embodiments, the proximal head 108 is larger in diameter than the rest-state diameter of the bore 122 at the distal end 140 of the skirt 126. Referring to FIG. 2, the slots 136 facilitate outward flexibility of the skirt 126 as indicated by arrows 158. Thus, the skirt 126 is adapted to diametrically expand from the rest-state to receive the proximal head 108 that may be larger in diameter than the bore 122 at the distal end 140 of the 126 skirt in the rest-state.

In use, the shaft 112 is advanced into bone by utilizing a tool having a tip accommodated by the recess 118 as known in the art. In one embodiment of a method for implantation of a polyaxial bone screw including a distal loading receiver, the shaft 112 is advanced into the bone as a first step in the method. Next, the retaining ring 106 is placed over the proximal head 108 of the shaft 112 such that the retaining ring 106 is disposed around the shaft 112. The bore 122 of the body member 104 is coaxially aligned with the proximal head 108 of the shaft 112. As discussed hereinabove, the proximal head 108 may have a diameter that is larger than the bore 122 at the distal end 140 of the skirt 126. However, the slots 136 allow the skirt 126 to diametrically expand to allow the proximal head 108 entry into the bore 122.

Following alignment, the distal end 140 of the skirt 126 is forced into a proximal end 160 of the retaining ring 106, as indicated by arrows 162 in FIG. 2 such that the slots 136 accommodate the walls 152. Ultimately, as the body member 104 is pushed further into the retaining ring 106, the ribs 138 snap into and are thereby accommodated by the recesses 148 to attach the body member 104 to the retaining ring 106.

Note that both the polyaxial bone screw 102 and the retaining ring 106 are loaded into or onto the body member 104 from a distal side thereof. Such distal loading allows the shaft 112 to be implanted first without interference from the body member.

In embodiments where the retaining ring 106 includes the annular wall 156 and the annular wall 156 has an inner diameter smaller than that of the proximal head 108, the first step of the embodiment of the method for implantation is to position the distal end 116 of the shaft 112 at the site of implantation and within the annular wall 156. In this method, following advancement of the shaft 112 into the bone, the bore 122 of the body member 104 is aligned over the proximal head 108, and the body member 104 and the retaining ring 106 are forced toward one another for mutual attachment.

A further embodiment of a distal loading receiver 200 for a polyaxial bone screw 102 includes the body member 104, the retaining ring 106, and a bushing 202, as illustrated in FIG. 3. The bushing 202 includes a circumferential wall 220 defining a bore 222 disposed along the longitudinal axis 124 and through the bushing 202. The circumferential wall 220 includes a second pair of oppositely disposed proximally opening slots 232 that each includes a rounded distal end 234 for accommodation of a fixation rod (not shown) therein. A pair of oppositely disposed resilient tabs 242 is disposed at a proximal end 260 of the bushing 202. In one embodiment, the tabs 242 can snap into and thereby be accommodated by the one or more apertures 142 disposed through the circumferential wall 120 to secure the bushing 202 within the body member 104. In another embodiment, the tabs 242 can snap between and thereby be accommodated by the threads or ratchets 144 disposed on an inner surface of the bore 122 to secure the bushing 202 within the body member 104.

The circumferential wall 220 further includes a second skirt 226 disposed opposite the proximal end 260. The second skirt 226 defines a pair of oppositely disposed distally opening slots 236, which provide axial flexibility to the bushing 202. When the bushing 202 is secured within the body member 104 and the distal loading receiver 200 is assembled on the bone screw 102, the second skirt 226 is adapted to abut a periphery of the proximal head 108 of the bone screw 102. Examples of bushings 202 that may be useful in the current invention may be found in Purcell et al. U.S. Patent Application Publication No. 2008/0243189 and Purcell et al. U.S. Pat. No. 7,377,923.

Another method for implanting a polyaxial bone screw including a distal loading receiver is similar to the method described hereinabove with regard to FIG. 2, except for the following differences. In this embodiment, the bushing 202 is introduced into the distal end 140 of the body member 104, as indicated by arrow 262 in FIG. 3. The bushing 202 may be secured within the body member 104 via cooperation of the tabs 242 and the apertures 142, the threads or ratchets 144, or by other methods of attachment as may be known in the art. Next, with the bushing 202 held inside the body member 104, the bore 122 of the body member 104 is coaxially aligned with the proximal head 108 of the shaft 112. Following alignment, the distal end 140 of the skirt 126 is forced into a proximal end 160 of the retaining ring 106, as indicated by arrows 264 in FIG. 3 such that the slots 136 accommodate the walls 152. In some embodiments, the busing 202 is configured to move distally, such as during compression by a fixation rod, and the second skirt 226 slides distally over proximal head 108 of the bone screw 102 and engages the bore 122 within the skirt 126 to lock the head 108 in place.

An improved distal loading receiver for a polyaxial bone screw for a spinal immobilization system is presented. The distal loading receiver may be attached over a head of a bone screw subsequent to advancement of a shaft of the bone screw into bone. Such subsequent attachment facilitates implantation of the shafts closer together than would otherwise be practical due to the presence of a receiver attached to each shaft before such implantation. Such a distal loading receiver also facilitates assembly of the receiver over the head in situ.

It will be appreciated by those skilled in the art that changes could be made to the embodiments described hereinabove without departing from the broad concepts disclosed therein. It is understood, therefore, that this disclosure is not limited to the particular embodiments disclosed, but it is intended to cover modifications that may include a combination of features illustrated in one or more embodiments with features illustrated in any other embodiments. Various modifications, equivalent processes, as well as numerous structures to which the present disclosure may be applicable will be readily apparent to those of skill in the art to which the present disclosure is directed upon review of the present specification. Accordingly, this description is to be construed as illustrative only and is presented for the purpose of enabling those skilled in the art to make and use the distal loading receiver for a polyaxial bone screw described herein and to teach the best mode of carrying out the same.

Example embodiments of the methods and systems of the present invention have been described herein. As noted elsewhere, these example embodiments have been described for illustrative purposes only, and are not limiting. Other embodiments are possible and are covered by the invention. Such embodiments will be apparent to persons skilled in the relevant art(s) based on the teachings contained herein. Thus, the breadth and scope of the present invention should not be limited by any of the above-described exemplary embodiments, but should be defined only in accordance with the following claims and their equivalents.

The invention claimed is:

1. A distal loading receiver for a polyaxial bone screw, comprising:
   a body member having a circumferential wall defining a bore disposed longitudinally through the body member;
   a skirt depending from a distal end of the body member, wherein the skirt defines one or more distally opening slots and an abluminal surface of the skirt includes one or more transverse ribs proximate to a distal end of the skirt; and a retaining ring including a luminal surface having one or more transverse recesses proximate to a distal end of the luminal surface and one or more walls extending inwardly from the luminal surface;
wherein distal open ends of the slots receive the walls such that the walls fit within the slots and the recesses accommodate the ribs to attach the body member to the retaining ring when the distal end of the skirt is inserted into a proximal end of the retaining ring.

2. The distal loading receiver of claim 1, wherein the skirt is adapted to expand from a rest state to receive a bone screw having a proximal head that is larger in diameter than the bore at the distal end of the skirt in the rest state.

3. The distal loading receiver of claim 2, wherein the circumferential wall includes a pair of oppositely disposed proximally opening slots that each includes a rounded distal end.

4. The distal loading receiver of claim 3, further comprising a bushing disposed within the bore and including a second pair of oppositely disposed proximally opening slots and a second distally depending skirt, wherein the second pair of oppositely disposed proximally opening slots is adapted to accommodate a fixation rod, and the second distally depending skirt is adapted to abut a periphery of the proximal head.

5. The distal loading receiver of claim 4, further including the bone screw having a proximal head that is larger in diameter than the bore at the distal end of the skirt in the rest state.

6. The distal loading receiver of claim 1, wherein an abluminal surface of the skirt depending from the distal end of the body member is diametrically constricted relative to the body member.

7. The distal loading receiver of claim 1, wherein the retaining ring includes an annular wall extending inwardly from the luminal surface distal to the transverse recesses.

8. A polyaxial screw assembly, comprising:
a polyaxial screw having a proximal head and a threaded shaft;
a body member having a circumferential wall defining a bore for receiving the polyaxial screw, wherein the circumferential wall includes a first pair of oppositely disposed proximally opening slots that each includes a rounded distal end;
a first skirt depending from a distal end of the body member, wherein the first skirt defines one or more distally opening slots and an abluminal surface of the first skirt includes one or more transverse ribs proximate to a distal end of the first skirt; and
a retaining ring including a luminal surface having one or more transverse recesses proximate to a distal end of the luminal surface and one or more walls extending radially inward from the luminal surface;
wherein distal open ends of the slots receive the walls such that the walls fit within slots and the recesses accommodate the ribs to attach the body member to the retaining ring when the distal end of the first skirt is inserted into a proximal end of the retaining ring.

9. The polyaxial screw assembly of claim 8, further comprising a bushing disposed within the bore and including a second pair of oppositely disposed proximally opening slots and a second distally depending skirt, wherein the second pair of oppositely disposed proximally opening slots is adapted to accommodate a fixation rod, and the second distally depending skirt is adapted to abut a periphery of a proximal head of a bone screw.

10. The polyaxial screw assembly of claim 8, wherein the first skirt is adapted to expand from a rest state to receive the polyaxial screw, wherein the proximal head is larger in diameter than the bore at the distal end of the skirt in the rest state.

11. The polyaxial screw assembly of claim 8, wherein an abluminal surface of the first skirt is diametrically constricted relative to the body member.

12. The polyaxial screw assembly of claim 8, wherein the retaining ring includes an annular wall extending inwardly from the luminal surface distal to the transverse recesses.

13. A method for assembling a polyaxial screw assembly that includes a polyaxial screw, a body member, and a retaining ring, comprising the steps of:
placing the retaining ring over a proximal head of the polyaxial screw, the retaining ring including a luminal surface having one or more recesses proximate to a distal end of the luminal surface and one or more walls extending inwardly from the luminal surface;
aligning a bore of the body member with the proximal head of the polyaxial screw, the body member having a circumferential wall defining the bore disposed longitudinally through the body member;
forcing a distal end of a skirt depending from a distal end of the body member into a proximal end of the retaining ring, the skirt defining one or more distally opening slots and an abluminal surface of the skirt including one or more transverse ribs proximate to a distal end of the skirt; and
inserting the polyaxial screw into a vertebra prior to placing the ring over the proximal head, aligning the bore of the body member with the proximal head, and forcing the distal end of the skirt into the ring,
wherein the slots of the skirt accommodate the walls of the retaining ring and recesses of the retaining ring accommodate the ribs of the skirt to attach the body member to the retaining ring.

14. The method of claim 13, further comprising the step of inserting a bushing into the distal end of the body member, the bushing including a second pair of oppositely disposed proximally opening slots and a second distally depending skirt, wherein the second pair of oppositely disposed proximally opening slots is adapted to accommodate a fixation rod.

* * * * *